United States Patent [19]
Coplot et al.

[11] Patent Number: 4,564,453
[45] Date of Patent: Jan. 14, 1986

[54] METHOD AND APPARATUS FOR THE DETECTION OF TOXIC SUBSTANCES IN WASTE WATER FEEDING A BIOLOGICAL TREATMENT PLANT

[75] Inventors: Daniel Coplot, Franconville; Georges Picon, Gennevilliers, both of France

[73] Assignee: Atochem (Societe Anonyme Styled), France

[21] Appl. No.: 572,465

[22] Filed: Jan. 20, 1984

[30] Foreign Application Priority Data

Jan. 24, 1983 [FR] France ................................ 83 01027

[51] Int. Cl.$^4$ .......................... C02F 3/12; C12M 1/36; G01N 33/18
[52] U.S. Cl. ..................... 210/614; 210/85; 210/96.1; 210/745; 435/32; 435/291; 436/55; 436/62; 436/138
[58] Field of Search ...................... 210/614, 96.1, 620, 210/625, 626, 627, 745, 746, 85; 435/289, 291, 32; 436/62, 138, 55

[56] References Cited

U.S. PATENT DOCUMENTS

| | | | |
|---|---|---|---|
| 3,986,932 | 10/1976 | Brushwyler et al. | 210/614 |
| 4,162,195 | 7/1979 | Solyom et al. | 210/614 |
| 4,260,490 | 4/1981 | Moss et al. | 210/620 |
| 4,329,232 | 5/1982 | McKenna | 210/614 |

FOREIGN PATENT DOCUMENTS

| | | |
|---|---|---|
| 0009580 | 4/1982 | European Pat. Off. . |
| 2951707 | 7/1981 | Fed. Rep. of Germany ........ 436/62 |
| 3128439 | 2/1983 | Fed. Rep. of Germany ...... 210/614 |
| 1567181 | 5/1969 | France . |
| 1567182 | 5/1969 | France . |
| 2067184 | 8/1971 | France . |
| 2266885 | 10/1975 | France . |
| 2428842 | 1/1980 | France . |
| 747826 | 7/1980 | U.S.S.R. ............................ 210/614 |
| 861343 | 9/1981 | U.S.S.R. ............................ 210/614 |

Primary Examiner—Benoit Castel
Attorney, Agent, or Firm—Brumbaugh, Graves, Donohue & Raymond

[57] ABSTRACT

Waste water to be analyzed is brought into a reactor continuously supplied with samples of activated sludge taken from the biological treatment plant; oxygen is also constantly supplied to the reactor and the content of oxygen dissolved inside the reactor is measured in order to automatically regulate the waste water flow admitted into the reactor in relation the measured value of dissolved oxygen content and thus keep the load applied to the reactor substantially constant; a toxicity alarm is released in case of abnormal reduction of respiration when the waste water admission flow is maximum.

8 Claims, 6 Drawing Figures

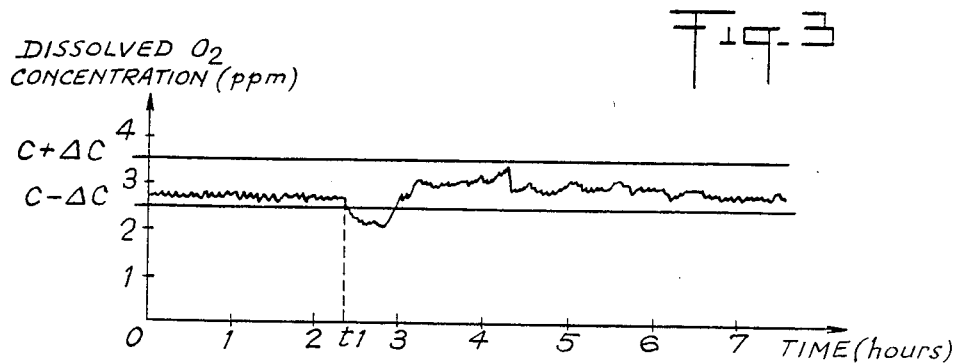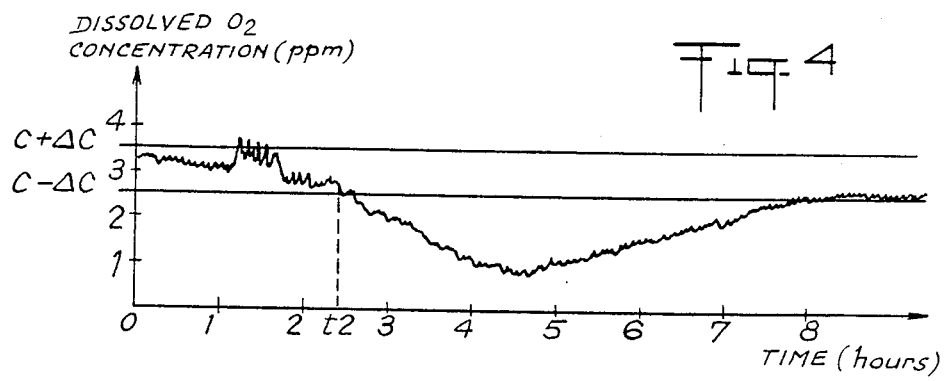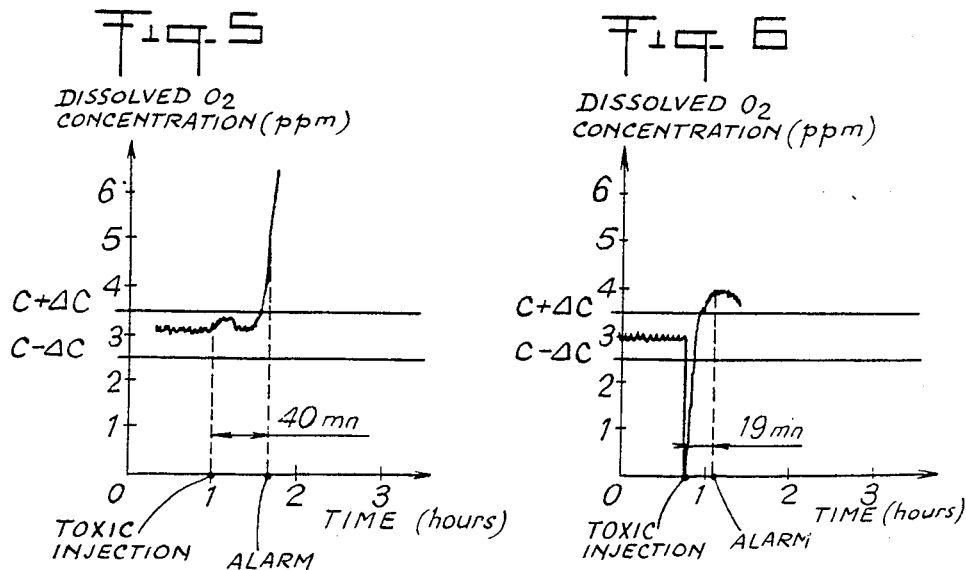

METHOD AND APPARATUS FOR THE DETECTION OF TOXIC SUBSTANCES IN WASTE WATER FEEDING A BIOLOGICAL TREATMENT PLANT

BACKGROUND OF THE INVENTION

The present invention relates to a method for the detection of toxic substances in the waste water supplied to a biological treatment plant.

In such plants where waste waters are biologically treated, the effluents are brought into contact with micro-organisms which metabolize the dissolved organic materials in the presence of oxygen.

The activity of these micro-organisms may be partly or completely inhibited, when the waste waters contain a concentration of toxic materials such that the purifying biomass becomes poisoned, thus reducing or stopping the purifying process.

When these toxic materials are not detected soon enough, the entire biomass of the plant may become poisoned and it then takes several weeks before the purifying plant can resume its activity. The advantage of detecting the presence of toxic substances in waste waters before they can affect the purifying plant, is therefore imperative.

Many methods of detecting toxic substances are already known and used, such as for example methods based on respirometric measurements: wherein toxic substances modify the metabolism of the micro-organisms with which they come into contact, and the variation of metabolic activity can be detected with great sensitivity by studying one essential function which is, respiration.

For example, according to the method described in French Patent Application No. 2,428,842, the liquid for testing is oxygen-saturated and introduced into a reactor where it is mixed with a fraction of bacterial culture and with a nutrient. The culture is so prepared as to have a bacterial aqueous suspension with stable characteristics. The liquid is introduced at the inlet to a reactor formed by a thin long tube and the oxygen content is measured at the reactor outlet, situated at the other end of the tube; the peaks detected in the recordings of the oxygen content measured value indicate the presence of toxic substances. A similar method is described in French Pat. No. 2 266 885 consisting in oxygen-saturating part of the effluent to be tested and causing it to flow through a bacterial filter, at the outlet of which the dissolved oxygen is measured. Where the consumption of oxygen is too low a toxicity alarm installation is activated. Seeding of the reactor is periodically renewed and dilution of the effluent with a nutrient solution becomes necessary when effluent load variations are too great. With such methods, the micro-organisms used in the reactor can react differently from the micro-organisms present in the purifying plant. Moreover, the dilution of the effluent with a nutrient solution entails a dilution of the toxic substances which delays its detection.

In the method according to U.S. Pat. No. 4,260,490, the respiration measured on an activated sludge sample taken from the treatment plant is compared with the respiration measured on an activated sludge sample from the plant having the effluent to be analyzed. If the oxygen consumption speed difference between the samples is below a certain value, determined with a non-toxic effluent used as reference, the monitored effluent is deemed toxic. If on the contrary, said difference is higher than the value determined with an effluent of average oxygen biological intake, the oxygen intake is greater. A computer works out the results of the respirometric tests and if necessary releases a signal in the case of toxicity. This particular method is therefore a discontinuous method which, in addition to computer means, requires two oxygen sensing means as well as two analyzers.

According to yet another method of the type described in French Pat. Nos. 1,567,181, 1,567,182 and 2,067,184, a reactor is used, which reactor receives a certain quantity of activated sludge from the plant oxygenated by injection of compressed air. When these sludge samples reach a constant respiration, a sample of effluent to be analyzed is injected. The oxygen intake from that particular moment is continuously measured and a computer gives the metabolizing curve. Then, if during subsequent measurements the respiration falls below a preset value, the presence of toxic substances is highly probable. This is therefore a discontinuous monitoring method.

Finally, European patent application EP No. 0,009,580 discloses a system permitting control of a biological purifying installation using a measuring device which can receive a mixture or suspension of waste water and recycled sludge collected before its introduction into the basin of the installation. The measuring device comprises a reactor, into which the suspension is introduced and oxygen-saturated, and a measuring cell set apart from the reactor and designed to measure oxygen consumption. The distance between the reactor and the measuring cell is so defined as to correspond to a pre-set reaction period. If the oxygen consumption measurement goes beyond or below first pre-set maximum and minimum thresholds, the flow of recycled sludges to the purifying plant is adjusted. If a second minimum threshold, lower than the first is crossed, this is a sign of poisoning.

SUMMARY OF THE INVENTION

The object of the present invention is to provide a method and device specifically designed to continuously monitor the toxicity of waste waters, in conditions as near as possible to the purifying plant operating conditions, with immediate signalling upon the appearance of toxins.

More specifically, the invention relates to a method wherein the waste water to be tested is brought into contact with activated sludge samples taken from the biological treatment plant, inside a reactor which is constantly supplied with oxygen. The quantity of oxygen dissolved in the reactor is measured with a view to releasing a toxicity alarm when an abnormal reduction of respiration occurs. In accordance with the invention, the reactor is continuously supplied with activated sludge samples from the plant. The quantity of oxygen dissolved in the reactor is compared to permanently preset maximum and minimum values. The flow of waste water supplied to the reactor is automatically regulated by being reduced or increased whenever the measured content value is below the preset minimum value or above the preset maximum value, in order to keep substantially constant the load applied to the reactor. The toxicity alarm is released whenever the measured content exceeds the maximum value when the waste water supplied to the reactor is at a maximum.

Continual supply of the reactor with sludge samples from the treatment plant and with waste water intended for said plant results in approximating the normal running conditions of the plant. Also, by automatically controlling the flow of waste water the applied polluting load is kept substantially constant and any abnormal reduction of respiration may be attributed with certainty to the presence of toxic substances in the waste water. The alarm is released if it becomes impossible to stabilize the quantity of dissolved oxygen to a given level just by altering the reactor load. Thus, the fact of increasing the waste water flow rate whenever the quantity of dissolved oxygen decreases, enables to speed up the detection of toxicity.

A further object of the present invention is to provide an apparatus for carrying out said method.

This object is achieved by an apparatus comprising a reactor designed to contain activated sludge samples taken from the biological treatment plant, means of supplying the reactor with oxygen, means of supplying the reactor with waste water to be analyzed, means of measuring the quantity of oxygen dissolved in the reactor and an alarm device connected to the measuring means to release a toxicity alarm signal in case of abnormal reduction of the respiration. Accordingly, the apparatus of the present invention provides a means of permanently supplying the reactor with activated sludge samples taken from the plant; a regulating means comprising a comparator circuit designed to compare the measured value of the dissolved oxygen content to maximum and minimum values, a control circuit for controlling the pump supplying waste water to the reactor; and a selector circuit connected to the comparator circuit and designed to apply a variable signal to the control circuit, depending on whether the measured oxygen content is less than said minimum value, or more than said maximum value or between the two.

BRIEF DESCRIPTION OF THE DRAWINGS

The present invention will be more readily understood on reading the following description with reference to the accompanying drawings.

FIGS. 3 to 6 are curves illustrating the variations in the dissolved oxygen content of the reactor in the apparatus in response to load variations or to the appearance of toxic substances in the waste water to be monitored.

DESCRIPTION OF THE PREFERRED EMBODIMENT

Figure 1:
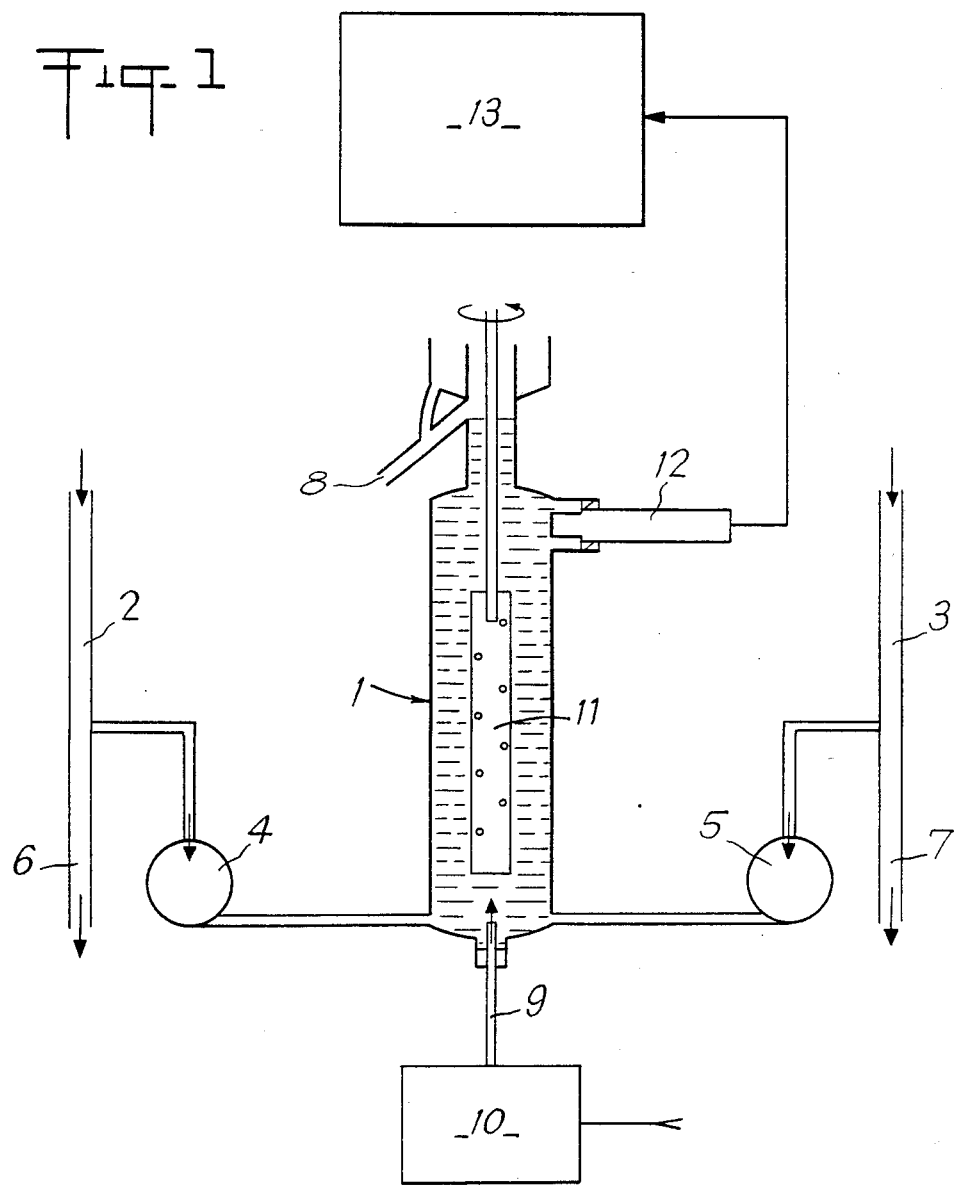
FIG. 1 is a schematic diagram of an embodiment of the apparatus according to the present invention.

The apparatus schematically illustrated in FIG. 1 comprises a reactor 1 supplied with waste water to be analyzed for toxic substances, and activated sludge samples taken from a biological treatment plant (not shown) used for purifying the monitored waste water.

The biological sludge samples can be taken from the activated sludge basins or, preferably, from the circuit in which the sludge is recycled after being concentrated in the plant decanter. Samples of the waste water to be monitored are taken upstream of the plant or of the homogenization basin, if any. The apparatus for detecting toxic substances is preferably installed proximate to where the samples of sludge and waste water are taken so that the time elapsing between the collection of the samples and their arrival to the apparatus is no more than a few minutes. To shorten this time as much as possible, and to avoid any deposit in the pipes supplying the waste water and sludge, fast supply loops, 2 and 3 respectively, are created on the circuit. Hydrostatic pressure or the delivery pressure from pumps already installed in the plant, may be used: for example a sludge recycling pump. Branch-connections are made on these loops at the level of the apparatus, to supply the reactor 1 with waste water via peristaltic pump 4, and with sludge, via peristaltic pump 5. Any excess of waste water or sludge or any overflow from reactor 1 are recycled at the head of the plant via respective pipes 6, 7, 8. The reactor is supplied continuously with activated sludge and waste water to be monitored.

Oxygen is also constantly fed in the reactor 1 by bubbling of compressed air via a porous or drawn out tube 9 traversing the bottom of the reactor. The pressure and flow rate of the compressed air brought into tube 9 are regulated and controlled by regulating means 10. Dissolving of the oxygen is helped by agitator 11 rotating at as constant a speed as possible.

An oxygen sensor 12, (polarographic type) supplies a signal which represents the amount of oxygen dissolved in the reactor. Sensor 12 is located near the output of the reactor 1 at the upper part thereof. The output signal of the sensor 12 is applied to a regulation and alarm device 13 described in more detail with reference to FIG. 2.

The variation of dissolved oxygen concentration in the reactor determines whether the applied polluting charge is normal, high, low or shows any toxicity, depending on whether said dissolved oxygen concentration remains stable, decreases or increases.

According to a characteristic of the present invention, the waste water supply flow to the reactor 1 is controlled in relation to the measured value of the dissolved oxygen concentration. If the concentration decreases and becomes less than a preset minimum threshold value, which indicates an increase of the applied charge, the flow of waste water is reduced. If on the contrary, the concentration increases and exceeds a preset maximum threshold value, which would indicate a reduction in the applied charge or in the toxicity, the flow of waste water is increased. In the case of a reduction of the charge, the dissolved oxygen concentration should return to a normal level. If toxic substances appear, the oxygen concentration will increase abnormally, which in turn releases an alarm, increasing the flow of waste water speeds up the detection process, which is one of the advantages brought by the invention.

To regulate the load applied to the reactor, the flow of waste water may be varied continuously or in stages. In this last case, several waste water flow values may be predetermined, the passage from one value to another being controlled in response to the minimum or maximum threshold values of dissolved oxygen concentration being crossed.

A comparison between the measured value of the concentration and the predetermined thresholds is made in the regulation and alarm device 13 which delivers signals designed in particular to control the pump 4 to fix the flow of waste water being brought to the reactor and when the need arises, to release a toxicity alarm.

This signal issued by the sensor 12 is amplified by an amplifier circuit 14 having an adjustable gain. After amplification, the signal is applied to the input 15a of a discriminator 15. Said circuit comprises three outputs 15s, 15s', 15s" which are activated when the amplitude of the signal at input 15e is respectively within a predetermined range [C−ΔC, C+ΔC], less than C−ΔC or more than C+ΔC. The value C is the middle of the range, and is adjustable by way of a potentiometer 16 forming a voltage divider between ground and a terminal of potential +V of the supply voltage and applying an adjustable voltage on a first adjusting input 15r of the discriminator 15. Likewise, the width 2ΔC of the range is adjustable by way of another potentiometer 17 forming voltage divider and applying an adjustable voltage on a second adjusting input 15r' of the discriminator. Said latter is a circuit known per se, found on the market as an integrated circuit, such as for example the circuit manufactured under reference TCA 965 by The West German Company SIEMENS.

The signal applied to the input of discriminator 15, is transmitted, after a further amplification by means of an amplifier circuit 18, to a recorder 19.

Outputs 15s, 15s', 15s" of the discriminator are respectively connected to the magnet coils of three Reed type relays 21, 22, 23, the movable contacts of which act as switches between ground and first respective NOR gates inputs 24, 25, 26. Diodes 27, 28, 29 in parallel on the coils of relays 21, 22, 23 protect outputs 15s, 15s', 15s".

The second inputs of gates 24, 25, 26 receive the signals appearing respectively on outputs Q of RS-type flip-flops 31, 32, 33. Said signals are in the form of pulses having the same frequency but of different durations. Thus, duration D2 of the pulses outputted by flip-flop 32 is more than duration D1 of the pulses outputted by flip-flop 31 but it is less than duration D3 of the pulses outputted by flip-flop 33, all these durations having adjustable preset values, as described hereinafter.

The outputs of gates 24, 25, 26 are connected via diodes 34, 35, 36 to the input of an amplifier circuit 37 of which the output energizes the magnetic coil of a relay 38. Said relay, when closed, enables to supply the motor 40 of pump 4. A hand-operated switch IP is connected in series with a diode 39 between a terminal of potential +V and the input of amplifier 37, in order to allow the manual control of pump 4.

Depending on whether relay 21, 22 or 23 is closed, the pump 4 is turned on at regular intervals for a respective period D1, D2 or D3 such as D1<D2<D3. Waste water supply flows, controlled respectively to "low", "normal" and "high", are thus directed into the reactor 1.

The movable contacts or relays 21, 22, 23 also act as switches, connected between ground and the first inputs of respective NOR gates 41 42, 43. Said first inputs are connected, on the one hand, to the first inputs of respective gates 44, 45, 46, also of the NOR type, and on the other hand, to a terminal of potential +V via respective resistors 47, 48, 49. The second inputs of gates 41, 42, 43 receive the signal applied to the input of amplifier 37 and the second inputs of gates 44, 45, 46 receive the same signal reversed by a gate 50.

The outputs of gates 41 to 46 are connected via resistors to the bases of respective transistors 51 to 56. The collector of each of said transistors is grounded via a resistor. An electroluminescent double diode 61 is connected between the transmitters of transistors 51 and 54 so that a red luminescence is transmitted when transistor 54 is conducting and transistor 51 is blocked. Conversely, a green luminescence will appear when transistor 51 is conducting and transistor 54 is blocked. The diode will not transmit when the two transistors 51 and 54 are in the same state.

Likewise, an electroluminescent double diode 62 is connected between the transmitters of transistors 53 and 56.

If the relay 21, 22, or 23 is closed, the gates 41, 44 or 42, 45 or 43, 46 are validated.

The control signal applied at the input to the amplifier 37 controls the red-lighting up of diodes 61, 62 or 63, whereas the absence of said signal controls the green-lighting up said diodes. Thus, depending on whether the lit diode is diode 61, 62 or 63, the real waste water supply flow to reactor 1 is "low", "normal" or "high". The red-lighting up of said diode indicates that the motor of the pump 4 is powered whereas its green-lighting up indicates that the motor of the pump 4 is not powered.

The signals applied to inputs R and S of flip-flops 31, 32, 33 are worked out as follows.

A signal having the frequency of the sector (50 Hz) is taken for example from the supply transformer and sent through a diode 71 to a shaping circuit constituted by two NOR gates 72-73 with hysteresis and connected in series. The square signal of 50 Hz outputted from gate 73 is applied to a frequency divider 74 producing a signal of period equal for example to 1/100th of a minute. This signal is applied to the counting input of a decimal counter-decoder 75 of which the carry-over output CO is connected to the counting input of a second decimal counter-decoder 76. Three coding wheels 81, 82, 83 each enable selection of any one of outputs 0 to 9 of the counter 75. Likewise, three coding wheels 81', 82', 83' each enable to select any one of outputs 0 to 9 of counter 76.

The outputs selected by coding wheels 81 and 81' are interconnected by an AND-type gate 84 formed with diodes, the output of which is connected to the input S of flip-flop 31. Likewise, the outputs selected by coding wheels 82 and 82' are interconnected via an AND gate 85, the output of which is connected to the input S of flip-flop 32, and the outputs selected by coding wheels 83 and 83' are interconnected by an AND gate 86 the output of which is connected to the input S of flip-flop 33. Another AND gate 87 has its inputs connected to outputs 0 of counters 75, 76 and its output connected to inputs R of flip-flops 31, 32 and 33.

Thus the pulses produced by flip-flops 31, 32, 33 have, in the illustrated example, a period of 1 min. and durations D1, D2, D3 expressed in 1/100th of a minute and selected by the pairs of coding wheels 81-81', 82-82' and 83-84'. A one-minute cycle is thus produced for controlling the motor of the waste water pump, which cycle has a WORK-STOP cyclic ratio varying between 0 and 99% of the time.

The one-minute signal outputted by the carry-over output of counter 76 is applied to the counting input of a decimal counter-decoder 91, the carry-over output of which is connected to another counter-decoder formed, for example, simply by a D-type flip-flop 92. The resetting inputs R of counter 91 and of flip-flop 92 are grounded via the switch formed by the movable contact of relay 23. A coding wheel 93 enables selection to any one of outputs 0 to 9 of counter 91 and a second coding wheel 94 enables selection of the value 1 or 0 by connection to the output Q of flip-flop 92 or with a terminal 99 of potential +V. The terminals thus selected are connected to the inputs of an AND-type gate 95 formed with diodes, the output of which is connected to the base of a transistor 96. The transmitter of said transistor is grounded and its collector is connected to a terminal of potential +V via the magnetic coil of a Reed-type relay 97. A protection diode 98 is connected in parallel on said coil.

The movable contact of relay 97 acts as a switch connected between a terminal of potential +V and, respectively, the counting-inhibiting input CI of counter 75, an electroluminescent diode 100 and the input of an amplifier circuit 101. Said latter has its output connected to the energization coil of a relay 102 whose closure controls the operation of a toxicity alarm circuit 103.

When relay 21 closes, inputs R of counter 91 and flip-flop 92 pass to zero and the output signals of counter 76 are counted by counter 91. If relay 21 remains closed for a period at least equal to the period displayed in minutes by the coding wheels 94 and 93, the toxicity alarm is released and the diode 100 lights up. The inhibition of counter 92 keeps the alarm on as long as said counter is not reset. If, on the contrary, the measured concentration returns to normal before the end of timing, relay 21 opens. Counter 91 is reset as well as flip-flop 92 and the output signals of counter 76 are no longer counted.

Figure 2:
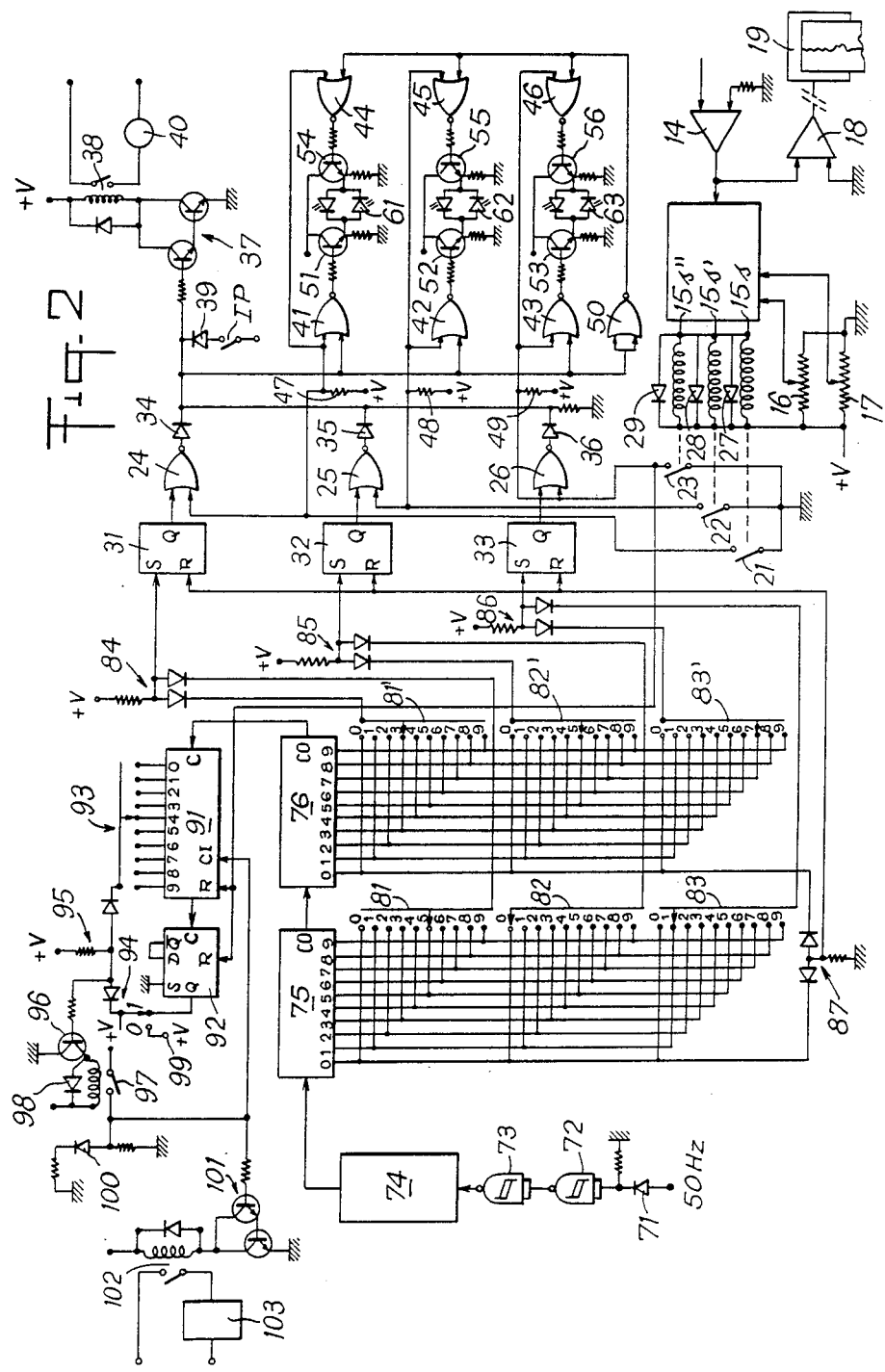
FIG. 2 is a diagram of the circuits utilized for regulating the waste water flow and of the alarm device shown in FIG. 1.

Obviously, the way in which the circuits described with reference to FIG. 2 work, is a direct result of the foregoing.

The set value C of the concentration of oxygen dissolved in the reactor and the acceptable difference $\Delta C$ above or below that value are controlled by the operator by means of potentiometers 16 and 17. With the coding wheels 81-81', 82-82' and 83-83', the operator selects also the values of the working periods of pump 4 for each WORK-STOP cycle thereof, i.e. the values of the "low" flow rate, "normal" flow rate, and "high" flow rate of waste water supply to the reactor. These controls being set, the reactor is filled by actuating the hand-operated switch IP of pump 4. Then, the output rate of pump 4 is controlled automatically by the output signal of discriminator 15, thus permitting regulation of the charge applied to the reactor. Diodes 61 to 66 inform the operator whether the waste rate is "low", "normal" or "high", meaning that the load is high, normal or low. It is thus possible, on the basis of that information, to regulate for example the oxygen flow into the treatment plant.

The operator also predetermines with coding wheels 93 and 94, the maximum time period after which the dissolved oxygen concentration, having exceeded the maximum value $C+\Delta C$ and caused the switching over of the pump output to its "high" value, should return within the tolerable limits, failing what the fact of maintaining the measured concentration to a level above $C+\Delta C$ is imputed to the appearance of toxic substances. In the illustrated example, said period may be set to between 0 and 19 minutes. With the method according to the invention, toxic substances are detected in a very short time because of the acceleration effect due to switching over to the "high" flow rate. Owing to this rapid detection, the necessary measures can be taken at the opportune moment to prevent any degradation of the biomass in the basins of the treatment plant, for example, the feeding of the basins with the waste water is interrupted.

FIGS. 3 to 6 illustrate the measured variations of dissolved oxygen concentration measured as a function of time, in the different tests conducted with the aforedescribed apparatus.

The set value for said concentration was selected to be equal to 3 ppm, plus or minus 0.5 ppm, as an acceptable possible difference. The reactor, having a capacity of 2.4 liters, was permanently supplied with samples of sludge taken at the input to the plant with a flowing rate of 5.7 l/hour and was ventilated by a constant airflow equal to about 1 l/hour. Selected "low", "normal" or "high" flow rate values were 110 ml/hr, 220 ml/hr, and 440 ml/hr. Timing of the toxicity alarm was fixed at 10 minutes.

FIG. 3 shows that an increase of the polluting load at time $t_1$ resulted in a reduction of the measured concentration. The reduction was temporary, and of relatively short duration due to compensation through regulation of the waste water flow as soon as the concentration dropped below the threshold of 2.5 ppm.

FIG. 4 shows that a very strong increase of load at time $t_2$ is compensated for in a longer period of time.

FIGS. 5 and 6 show the curves of concentration variation in the case of deliberate introduction of toxic substances, respectively sodium hypochlorite in concentration of 2.3 g of active chlorine per liter of waste water and tertiobutylcatechol at the rate of 1 g introduced in the reactor. In the first case, the alarm was released 40 mins. after the introduction. In the second case, there was first a rapid consumption of oxygen due, very likely, to the oxidation of tertiobutylcatechol in very toxic quinones; after what the dissolved oxygen concentration increased very rapidly, causing the release of the alarm 20 minutes after the introduction of tertiobutylcatechol into the reactor.

According to the embodiment of the apparatus according to the invention described hereinabove, only three levels of waste water flows are set. Obviously, the number of these levels can be increased, especially if great load variations have to be compensated. For example, a "very low" and a "very high" flow rate can be selected. It could also be possible to make finer adjustments of the load by varying the waste water flow, between a minimum and a maximum, with very small increases, continuously if necessary, as a function of the dissolved oxygen measured concentration. In all cases, the toxicity alarm is released when it is impossible to keep the oxygen content equal to or below a preset maximum value and when the waste water flow is at a maximum.

The invention is in no way limited to the description given hereinabove and on the contrary covers any modifications that can be brought thereto without departing from its scope or its spirit.

What we claim is:

1. A method for detecting toxic substances in the waste water supplied to a biological treatment plant wherein the waste water is brought in contact with activated sludge samples taken from the biological treatment plant inside a reactor, comprising the steps of:
   continuously supplying the reactor with activated sludge samples from the plant;
   supplying the reactor with waste water to be analyzed;
   continuously supplying the reactor with oxygen;
   measuring the quantity of oxygen dissolved in the reactor;
   comparing the measured quantity of oxygen dissolved in the reactor to selected maximum and minimum values;

regulating the flow of waste water supplied to the reactor by respectively reducing and increasing the waste water flow when the measured dissolved oxygen content value is respectively below the selected minimum value and above the selected maximum value in order to maintain the load applied to the reactor substantially constant; and activating a toxicity alarm when the measured content exceeds said maximum value and when the waste water supply to the reactor reaches a selected water flow rate maximum.

2. A method as claimed in claim 1, wherein the step of activating the toxicity alarm comprises activating the alarm when the measured dissolved oxygen content remains above said selected maximum value for a selected time period commencing when the waste water supply flow to the reactor reaches its selected water flow rate maximum.

3. A method as claimed in claim 1 or 2, wherein the step of regulating the waste water supply flow to the reactor comprises regulating the supply flow in stages between a selected minimum and the selected maximum water flow rate.

4. A method as claimed in claim 1 or 2, wherein the step of regulating the waste water supply flow to the reactor comprises regulating the waste water supply flow continuously throughout a range between a selected minimum and the selected maximum water flow rate.

5. An apparatus for detecting toxic substances in the waste water supplied to a biological treatment plant, comprising:

a reactor;

pump means including a conduit for supplying the reactor with activated sludge samples taken from the plant;

pump means including a conduit for supplying the reactor with waste water to be analyzed;

means for supplying the reactor with oxygen;

means for measuring the quantity of oxygen dissolved in the reactor;

regulating means comprising a comparator for comparing the measured value of the dissolved oxygen content to selected maximum and minimum oxygen values, a control circuit means for controlling the waste water pump means by respectively increasing and decreasing the flow rate of waste water to the reactor, a selector circuit connected to the comparator circuit for applying a variable signal to the control circuit to decrease the flow rate when the measured oxygen content is less than said minimum value, and to increase the flow rate when the measured oxygen content is more than said maximum value.

6. An apparatus as claimed in claim 5, wherein said selector circuit has means for producing said variable signal having pulses of fixed period and variable duration.

7. An apparatus as claimed in claim 5 or 6, wherein said apparatus further comprises an adjustable timing circuit means for activating an alarm circuit when the waste water supply flow to the reactor remains above a selected maximum value for a selected time period due to an increase in the measured dissolved oxygen content above the selected maximum value, and for resetting the alarm circuit when said measured content returns to under said maximum value before said selected time period elapses.

8. An apparatus as claimed in claim 5 or 6, wherein the means for supplying waste water and activated sludge to the reactor respectively comprise means for supplying waste water and activated sludge at a relatively fast supply rate in order to detect toxic substances quickly and to minimize backup and deposit of sludge being supplied to the reactor.

* * * * *